US012751603B2

(12) United States Patent
Dong et al.

(10) Patent No.: US 12,751,603 B2
(45) Date of Patent: Oct. 6, 2026

(54) ROTATABLE 3D ENDOSCOPE AND IMAGING SYSTEM WITH INTEGRATED DESIGN OF OPTICAL SYSTEM AND IMAGING UNIT

(71) Applicant: BEIJING FANXING GUANGDIAN MEDICAL TREATMENT EQUIPMENT CO., LTD, Beijing (CN)

(72) Inventors: Guoqing Dong, Beijing (CN); Qi Li, Beijing (CN)

(73) Assignee: BEIJING FANXING GUANGDIAN MEDICAL TREATMENT EQUIPMENT CO., LTD., Beijing (CN)

( * ) Notice: Subject to any disclaimer, the term of this patent is extended or adjusted under 35 U.S.C. 154(b) by 274 days.

(21) Appl. No.: 18/516,207

(22) Filed: Nov. 21, 2023

(65) Prior Publication Data

US 2024/0398214 A1 Dec. 5, 2024

(30) Foreign Application Priority Data

May 29, 2023 (CN) ......................... 202310613549.7
May 29, 2023 (CN) ......................... 202321327712.5
(Continued)

(51) Int. Cl.
*A61B 1/00* (2006.01)
*A61B 1/05* (2006.01)

(52) U.S. Cl.
CPC ...... *A61B 1/00194* (2022.02); *A61B 1/00128* (2013.01); *A61B 1/051* (2013.01)

(58) Field of Classification Search
CPC ............ A61B 1/00128; A61B 1/00194; A61B 1/00163; A61B 1/00188; A61B 1/00193; A61B 1/04; A61B 1/051; A61B 1/0051
See application file for complete search history.

(56) References Cited

U.S. PATENT DOCUMENTS 5,557,454 A * 9/1996 Takahashi .......... A61B 1/00193 348/45
2009/0096865 A1 4/2009 McKinley
(Continued)

FOREIGN PATENT DOCUMENTS

CN 201867583 U 6/2011
CN 106691589 A 5/2017
(Continued)

OTHER PUBLICATIONS

The first notification of preliminary opinions dated May 24, 2023; Appln. No. 202310613549.7.
(Continued)

*Primary Examiner* — Aaron B Fairchild
(74) *Attorney, Agent, or Firm* — Frank Gao, Esq.

(57) ABSTRACT

Embodiments of the present application disclose a rotatable 3D endoscope and imaging system with integrated design of an optical system and an imaging unit, which is invented to solve the problem of complex structure of 3D imaging endoscopes. The endoscope includes: an objective lens, disposed at the distal end of the endoscope, for collecting the light reflected by the target object to be observed outside the distal end of the endoscope; a relay optical system, disposed on the image side of the objective lens, for transmitting the light to a magnifying unit; a magnifying unit, disposed on the image side of the relay optical system, for transmitting the light to a first camera unit and a second camera unit; a first camera unit, disposed on the image side of the relay optical system, for receiving the light and generating the first image of the target object based on the light; a second camera unit, disposed on the image side of the relay optical system, for receiving the light and generating the second image of the target object based on the light. The embodiments of the present application are applicable to a video
(Continued)

scene using an endoscope to examine the abdomen, bladder, nasal cavity and skull base.

6 Claims, 5 Drawing Sheets

(30) Foreign Application Priority Data

Aug. 30, 2023 (CN) ......................... 202311105586.3
Aug. 30, 2023 (CN) ......................... 202322343543.0

(56) References Cited

U.S. PATENT DOCUMENTS

2014/0066700 A1* 3/2014 Wilson ............... A61B 1/00128
600/102
2018/0011308 A1* 1/2018 Zhao .................. A61B 1/00188
2021/0177246 A1 6/2021 Wang et al.
2022/0061643 A1 3/2022 Duckett, III

FOREIGN PATENT DOCUMENTS

CN 115919239 A 4/2023
CN 218832725 U 4/2023
JP 08-292379 A 11/1996

OTHER PUBLICATIONS

The second notification of preliminary opinions dated May 26, 2023; Appln. No. 202310613549.7.
First Chinese Office Action dated Jun. 30, 2023; Appln. No. 202310613549.7.
Second Chinese Office Action dated Jul. 19, 2023; Appln. No. 202310613549.7.
Chinese Decision of Rejection dated Aug. 1, 2023; Appln. No. 202310613549.7.
Chinese Reexamination Decision dated Oct. 8, 2023; Appln. No. 202310613549.7.
Chinese Notification to Grant Patent Right dated Oct. 16, 2023; Appln. No. 202310613549.7.

* cited by examiner

ROTATABLE 3D ENDOSCOPE AND IMAGING SYSTEM WITH INTEGRATED DESIGN OF OPTICAL SYSTEM AND IMAGING UNIT

TECHNICAL FIELD

The application relates to the technical field of medical diagnostic instruments, in particular to a 3D endoscope, an imaging system and an imaging method with integrated design of an optical system and an imaging unit.

BACKGROUND TECHNOLOGY

Medical diagnostic devices are devices or instruments that identify various medical conditions of patients, and can assist doctors in making accurate and timely diagnoses, so that doctors can effectively treat and manage diseases. An endoscope is a medical diagnostic instrument commonly used in minimally invasive surgery.

In order to realize 3D (Three Dimensional) imaging of the lesion area, the existing endoscope includes two optical paths, and each optical path includes an objective lens and a relay optical system. The structure of this endoscope that can realize 3D imaging is relatively complicated.

SUMMARY OF THE APPLICATION

In view of this, the embodiments of the present application provide a rotatable 3D endoscope, an imaging system and an imaging method with integrated design of an optical system and an imaging unit, so as to facilitate the realization of 3D imaging through a simple structure.

In order to achieve the above purpose, the embodiments of the present application provide the following technical solutions:

In the first aspect, the embodiment of the present application provides a rotatable 3D endoscope with integrated design of an optical system and an imaging unit, including: an objective lens, disposed at the distal end of the endoscope, for collecting the light reflected by the target object to be observed outside the distal end of the endoscope; a relay optical system, disposed on the image side of the objective lens, for transmitting the light collected by the objective lens at the distal end of the endoscope to the magnifying unit; a magnifying unit, disposed on the image side of the relay optical system, for transmitting the light collected by the objective lens at the distal end of the endoscope transmitted by the relay optical system to a first camera unit and a second camera unit; the first camera unit and the second camera unit are disposed side by side on the image side of the magnifying unit, and the clear apertures of the first camera unit and the second camera unit are located within the spot range of the emergent light of the magnifying unit; wherein, the first camera unit, for receiving the light collected by the objective lens at the distal end of the endoscope transmitted by the magnifying unit, and generating a first image of the target object based on the light; and the second camera unit, for receiving the light collected by the objective lens at the distal end of the endoscope transmitted by the magnifying unit, and generating a second image of the target object based on the light.

According to a specific embodiment of the present application, the first camera unit includes a first camera lens and a first imaging sensor; the magnifying unit and the first camera lens form a first magnification device, for forming the first image on the first imaging sensor with the light collected by the objective lens at the distal end of the endoscope transmitted by the optical system; the first image is a magnified image of the target object; the second camera unit includes a second camera lens and a second imaging sensor; the magnifying unit and the second camera lens form a second magnification device, for forming the second image on the second imaging sensor with the light collected by the objective lens at the distal end of the endoscope transmitted by the optical system; the second image is a magnified image of the target object.

According to a specific embodiment of the present application, the first camera unit and the second camera unit may rotate around the optical axis of the magnifying unit together.

According to a specific embodiment of the present application, the exit angle of light of the magnifying unit is greater than 15°.

According to a specific embodiment of the present application, the exit pupil distance of the magnifying unit is more than 5 mm.

According to a specific embodiment of the present application, the overall focal power of the magnifying unit is negative.

According to a specific embodiment of the present application, the magnifying unit includes a first magnifying unit, a second magnifying unit, and a third magnifying unit; wherein, the first magnifying unit includes a first lens with negative focal power and a second lens with positive focal power, the image side of the first lens and the object side of the second lens are cemented to each other to form a first cemented lens; the second magnifying unit includes a third lens with positive focal power and a fourth lens with negative focal power, the image side of the third lens and the object side of the fourth lens are cemented to each other to form a second cemented lens; the third magnifying unit includes a fifth lens with negative focal power and a sixth lens with negative focal power; the image side of the fifth lens and the object side of the sixth lens are cemented to each other to form a third cemented lens.

According to a specific embodiment of the present application, the rotatable 3D endoscope with integrated design of the optical system and the camera unit further includes: an insertion tube, the objective lens and the relay optical system are disposed in the insertion tube, wherein the objective lens is disposed at the distal end of the insertion tube; a magnifying unit support, the first end of the magnifying unit support is connected with the proximal end of the insertion tube, and the magnifying unit is disposed in the magnifying unit support; the camera unit support, the first end of the camera unit support is connected to the second end of the magnifying unit support; the first camera unit and the second camera unit are disposed side by side on the camera unit support; a handle, the handle is connected with the second end of the camera unit support.

According to a specific embodiment of the present application, the camera unit support may rotate around the optical axis of the magnifying unit.

According to a specific embodiment of the present application, the first end of the camera unit support is detachably connected to the second end of the magnifying unit; wherein, the end of the second end of the magnifying unit has a locking connection protrusion for inserting into the first end of the camera unit support; the first end of the camera unit support has a bayonet for accommodating the locking connection protrusion; the edge of the bayonet is provided with an elastic locking connection member; when the first end of the camera unit support is connected to the second end of the magnifying unit, the locking connection protrusion is inserted into the bayonet, and the elastic locking connection member clips the locking connection protrusion into the bayonet.

In the second aspect, an embodiment of the present application provides an endoscope imaging system, including: an endoscope, for obtaining the light reflected by the target object to be observed, and simultaneously generating a first image and a second image of the target object based on the light; an image processing unit, electrically connected to the endoscope, for generating a 3D image of the target object based on the first image and the second image; a display device, electrically connected to the image processing unit, for displaying the 3D image; wherein, the endoscope is a rotatable 3D endoscope with integrated design of an optical system and a camera unit as described in any one of the foregoing embodiments.

In a third aspect, an embodiment of the present application provides an endoscope 3D imaging method, including: collecting the reflected light of the target object to be observed through an objective lens; transmitting the light collected by the objective lens to an magnifying unit through a relay optical system; generating a first image of the target object by the magnifying unit and the first camera unit; generating a second image of the target object by the magnifying unit and the second camera unit; generating a first 3D image of the target object based on the first image and the second image.

According to a specific embodiment of the present application, the generating the first image of the target object through the magnifying unit and the first camera unit includes: magnifying the light spot on the image side of the relay optical system through the magnifying unit and a first camera lens in the first camera unit and forming the first image on the first imaging sensor in the first camera unit; the first image is a magnified image of the target object; the generating the second image of the target object through the magnifying unit and the second camera unit includes: magnifying the light spot on the image side of the relay optical system through the magnifying unit and a second camera lens in the second camera unit and forming the second image on the second imaging sensor in the second camera unit; the second image is a magnified image of the target object;

According to a specific embodiment of the present application, after generating the first 3D image of the target object, the endoscope 3D imaging method further includes: keeping the first camera unit and the second camera unit stationary, rotating the objective lens, the relay optical system and the magnifying unit together by an angle around the optical axis of the magnifying unit; generating a third image of the target object by the magnifying unit and the first camera unit; generating a fourth image of the target object by the magnifying unit and the second camera unit; generating a second 3D image of the target object based on the third image and the fourth image; wherein, the image content of the second 3D image has the same spatial orientation as the image content of the first 3D image.

Compared with the existing endoscope that realizes 3D imaging through two optical paths, each of which includes an objective lens and a relay optical system, the rotatable 3D endoscope, endoscope imaging system and endoscope 3D imaging method provided by the embodiments of the present application, forms an optical path by an objective lens and a relay optical system, and transmits the light reflected by the target object collected by the objective lens to the magnifying unit through the optical path, and the magnifying unit transmits the light reflected by the target object transmitted by the optical path to the first camera unit and the second camera unit, so as to realize 3D imaging of the target object according to the first camera unit and the second camera unit, and the structure is simpler.

In the fourth aspect, the present application also provides a 3D camera device, including: a concave lens, a first camera unit and a second camera unit; the concave lens, is used for magnifying the exit angle of the light passing through the concave lens; the first camera unit and the second camera unit are disposed on the image side of the concave lens, and the clear apertures of the first camera unit and the second camera unit are located within the spot range of the emergent light of the concave lens.

According to a specific embodiment of the present application, the first camera unit and the second camera unit are both camera units with an imaging resolution of 1080 P or 4 K.

According to a specific embodiment of the present application, the optical surface of the concave lens close to the first camera unit and the second camera unit is concave; and/or the optical surface of the concave lens far from the first camera unit and the second camera unit is concave.

According to a specific embodiment of the present application, the first camera unit and the second camera unit are disposed side by side and adjacent to each other on the image side of the concave lens.

According to a specific embodiment of the present application, the first camera unit and the second camera unit are capable of rotating together around the optical axis of the concave lens; or, the first camera unit, the second camera unit and the concave lens may rotate together around the optical axis of the concave lens.

According to a specific embodiment of the present application, the diameter of the concave lens is greater than the sum of the diameter of the lens of the first camera unit and the diameter of the lens of the second camera unit.

According to a specific embodiment of the present application, the axial distance between the first and second camera units and the concave lens is adjustable.

According to a specific embodiment of the present application, the axial distance between the concave lens and the eye lens is adjustable.

According to a specific embodiment of the present application, the size of the CMOS sensor of the first camera unit or the second camera unit is ⅓ inch, ⅙ inch, 1/10 inch, 1/11 inch or 1/18 inch.

An embodiment of the present application also provides a 3D optical endoscope, including: a 2D optical endoscopic imaging unit and a 3D camera device; the central axis of the 3D camera device is coaxial with the central axis of the 2D optical endoscopic imaging unit; the 3D camera device, disposed on the image side of the endoscopic imaging unit, is used to form a first image and a second image of the observation target located on the object side of the 2D optical endoscopic imaging unit from different angles of view through the 2D optical endoscopic imaging unit; wherein the 3D camera device is the 3D camera device described in any of the aforementioned embodiments.

According to a specific embodiment of the present application, the 2D optical endoscopic imaging unit is used to form a light spot capable of forming a real image of the observation target on the image side of the 2D optical endoscopic imaging unit.

According to a specific embodiment of the present application, the 3D endoscope includes a cylindrical connector, the first end of the connector is connected to the end of the image side of the endoscopic imaging unit, and the second end of the connector is connected to the end of the object side of the 3D camera device.

According to a specific embodiment of the present application, the axial distance between the 3D camera device and the 2D optical endoscopic imaging unit is adjustable.

According to a specific embodiment of the present application, the 2D optical endoscopic imaging unit is capable of rotating around the central axis of the 3D camera device; or, the 2D optical endoscopic imaging unit and the concave lens rotate together around the optical axis of the concave lens relative to the first camera unit and the second camera unit.

According to a specific embodiment of the present application, the 2D optical endoscopic imaging unit includes a lens or lens group for forming a real image of the observation target.

According to a specific embodiment of the present application, the 2D optical endoscopic imaging unit may be at least one 2D optical endoscopic imaging unit with a cross-sectional diameter of 2.7 mm, 3 mm, 4 mm, 5 mm, 8 mm, 10 mm or 12 mm.

In the 3D camera device provided by the embodiment of the present application, the first camera unit and the second camera unit are disposed on the image side of the concave lens, and the clear apertures of the first camera unit and the second camera unit are located within the spot range of the emergent light of the same concave lens, while the first camera unit and the second camera unit each have a certain field angle, and the light spot of the emergent light of the concave lens is located within the field angle range of the first camera unit and the second camera unit, so that the light of the target can enter the first camera unit and the second camera unit through the same concave lens. That is, the first camera unit and the second camera unit can simultaneously shoot the image of the target through the same concave lens. Due to the different positions of the first camera unit and the second camera unit relative to the concave lens, the images of the target shot simultaneously by the first camera unit and the second camera unit through the same concave lens have a certain parallax, thereby facilitating the subsequent generation of the 3D image of the target according to the image with parallax of the target obtained by the first camera unit and the second camera unit. Compared with the 3D camera device where the two camera units each realize 3D imaging through an optical light-guide structure, in the embodiment of the present application, the two camera units can shoot images of the same target with parallax through the same concave lens, and the structure is simpler.

DESCRIPTION OF DRAWINGS

In order to more clearly illustrate the technical solutions in the embodiments of the present application or the prior art, the following will briefly introduce the drawings that need to be used in the description of the embodiments or the prior art. Obviously, the accompanying drawings in the following description are only some embodiments of the present application. Those skilled in the art can also obtain other drawings based on these drawings without creative work.

DETAILED DESCRIPTION

Embodiments of the present application will be described in detail below in conjunction with the accompanying drawings.

It should be clear that the described embodiments are only some of the embodiments of the present application, not all of them. Based on the embodiments of the present application, all other embodiments obtained by persons of ordinary skill in the art without creative efforts fall within the protection scope of the present application.

In the description of the present application, the terms 'first' and 'second' are used for descriptive purposes only, and cannot be interpreted as indicating or implying relative importance or implicitly specifying the quantity of indicated technical features. Thus, the features defined as 'first' and 'second' may explicitly or implicitly include at least one of these features.

Embodiments of the present application provide a rotatable 3D endoscope, an endoscope imaging system, and an endoscope 3D imaging method with integrated design of an optical system and a camera unit, which facilitate the realization of endoscope 3D imaging through a simple structure.

The embodiments of the present application will be further described below with reference to FIG. 1 to FIG. 11.

Embodiment 1

Figure 1:
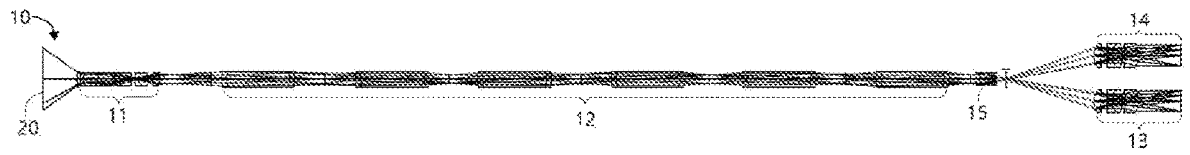
FIG. 1 is a structural schematic diagram of an embodiment of a rotatable 3D endoscope with integrated design of the optical system and the camera unit of the present application (only the optical path is shown)

FIG. 1 shows a structural schematic diagram of an embodiment of a rotatable 3D endoscope with integrated design of an optical system and a camera unit according to the present application. For clarity, only the optical path is shown in FIG. 1. Referring to FIG. 1, the endoscope 10 of this embodiment may include an objective lens 11, a relay optical system 12, a magnifying unit 15, a first camera unit 13 and a second camera unit 14.

Wherein, the objective lens 11, disposed at the distal end of the endoscope 10, is used for collecting light reflected by a target object 20 to be observed outside the distal end of the endoscope 10. The distal end of the endoscope 10 is the end of the endoscope 10 close to the target object 20 to be observed. The target object 20 to be observed may be lesions in the bladder, nasal cavity and stomach.

In some examples, the objective lens 11 may include an object lens (not shown in the figure) and a conversion prism (not shown in the figure), and a specific field angle of the objective lens 11 is obtained through the objective lens and the conversion prism, such as 0°, 12°, 30°, 70° or 90°, etc. The field of view of the objective lens can be changed by rotating the objective lens.

The relay optical system 12, disposed on the image side of the objective lens 11, is used for transmitting the light collected by the objective lens 11 at the distal end of the endoscope 10 to the magnifying unit 15. In other words, the objective lens 11 is disposed on the object side of the relay optical system 12 and can converge the light reflected by the target object 20 to be observed to the relay optical system 12. Wherein, the object side of the relay optical system 12 is the side of the relay optical system 12 close to the target object 20 to be observed.

The relay optical system 12 may be composed of multiple or multiple groups of rod lens, such as three or five groups of odd groups of rod lens. The number of rod lens groups depends on the length of the distance transmitted (working length of the endoscope). The longer the transmission distance, the more rod lens groups are needed, and vice versa.

Magnifying unit 15, disposed on the image side of the relay optical system 12, is used for transmitting the light collected by the objective lens 11 at the distal end of endoscope 10 transmitted by the relay optical system 12 to the first camera unit 13 and the second camera unit 14, so as to generate magnified images of the target object in the first camera unit 13 and the second camera unit 14 respectively.

The first camera unit 13 and the second camera unit 14 are disposed side by side on the image side of the magnifying unit 15, and the clear apertures of the first camera unit 13 and the second camera unit 14 are within the spot range of the emergent light of the magnifying unit.

The first camera unit 13 and the second camera unit 14 respectively have predetermined field angle. The clear apertures of the first camera unit 13 and the second camera unit 14 are located within the spot range of the emergent light of the magnifying unit 15, so that the light spot of the emergent light of the magnifying unit 15 is located within the field of view of the first camera unit 13 and the second camera unit 14. In this way, the first camera unit 13 and the second camera unit 14 can simultaneously collect the light spot of the emergent light of the magnifying unit 15, so as to simultaneously image the same target object from different orientations (or angle of view).

In other words, the light spot of the emergent light of the magnifying unit 15 is located within the field angle range of the first camera unit 13 and the second camera unit 14, so that the light reflected by the target can enter the first camera unit and the second camera unit through the same magnifying unit 15, that is, the first camera unit and the second camera unit can simultaneously shoot the image of the target through the same magnifying unit 15. Due to the different positions of the first camera unit and the second camera unit relative to the magnifying unit 15, the images of the target shot simultaneously by the first camera unit and the second camera unit through the same magnifying unit 15 have a certain parallax, thereby facilitating the subsequent generation of the 3D image of the target according to the image with parallax of the target obtained by the first camera unit and the second camera unit.

Specifically, the first camera unit 13, is used for receiving the light collected by the objective lens 11 at the distal end of the endoscope 10 transmitted by the magnifying unit 15 and generating a first image of the target object 20 based on the light.

The second camera unit 14, is used for receiving the light collected by the objective lens 11 at the distal end of the endoscope 10 transmitted by the magnifying unit 15, and generating a second image of the target object 20 based on the light.

In some embodiments, the objective lens 11, the relay optical system 12, may be used on the image side of the relay optical system 12, to form a light spot capable of forming a real image of the observation target. The light that forms the light spot of the real image can enter the first camera unit and the second camera unit to form the first image and the second image of the observation target respectively.

In other words, the first camera unit and the second camera unit can shoot the light spot forming the real image. Since the light spot is formed after the light of the observation target passes through the objective lens 11 and the relay optical system 12, based on the linear propagation of light, the first camera unit and the second camera unit are actually able to shoot the observation target through the relay optical system 12 and the objective lens 11, thereby obtaining the first image and the second image of the observation target.

In this embodiment, the objective lens, the relay optical system and the magnifying unit cooperate with the two camera units, and can form an integrated 3D endoscope optical system.

In particular, a magnifying unit cooperates with two camera units (the first camera unit 13 and the second camera unit 14) to form an integrated magnification imaging design, which can generate two magnified images of the same target object at the same time.

The endoscope provided by the embodiment of the present application forms an optical path by an objective lens and a relay optical system, and transmits the light reflected by the target object collected by the objective lens to the magnifying unit through the optical path, and the magnifying unit transmits the light reflected by the target object transmitted by the optical path to the first camera unit and the second camera unit; the first camera unit and the second camera unit are disposed side by side on the image side of the magnifying unit, and the clear apertures of the first camera unit and the second camera unit are located within the light spot range of the emergent light of the magnifying unit, so that the first camera unit and the second camera unit can simultaneously collect the light reflected by the same target object from different angles of view, and generate the first image and the second image respectively, so as to facilitate the subsequent generation of 3D (three dimensional) images of the target object according to the first image and the second image. Specifically, according to the first image and the second image, the parallax of observing the same target object under different field angles can be obtained later, so as to obtain the depth information of the target object through parallax calculation, and achieve better depth perception, so that 3D images of the target object can be generated. A 3D image may also be referred to as a three-dimensional image or a stereoscopic image.

Compared with the existing endoscope that realizes 3D imaging through two optical paths, each of which includes an objective lens and a relay optical system, the 3D endoscope provided by the embodiment of the present application forms an optical path by an objective lens and a relay optical system, and transmits the light reflected by the target object collected by the objective lens to the magnifying unit through the optical path, and the magnifying unit transmits the light reflected by the target object transmitted by the optical path to the first camera unit and the second camera unit, so as to realize 3D imaging of the target object according to the first camera unit and the second camera unit, and the structure is simpler.

In addition, compared to dispose two optical systems side by side at the front end of the endoscope, the embodiment of the present application only needs to dispose one optical system at the front end (also called the insertion end) of the endoscope, which can greatly reduce the size of the outer diameter of the front end of the endoscope, and helps to reduce the size of the surgical wound.

In some embodiments, the outer diameter of the front end of the endoscope may be 3 mm-6 mm. In one example, the outer diameter of the front end of the endoscope may be 3 mm; in another example, the outer diameter of the front end of the endoscope may be 4 mm; in yet another example, the outer diameter of the front end of the endoscope may be 5 mm; In still another example, the outer diameter of the front end of the endoscope may be 6 mm.

In some embodiments, after the objective lens 11 collects the light reflected by the target object to be observed outside the distal end of the endoscope, a first intermediate image (inverted real image) can be formed on the image side of the objective lens 11, and the relay optics system 12 transfers (or inverts) the first intermediate image 1:1 to the image side of the relay optical system 12 to form a second intermediate image.

After the first intermediate image is transferred through a set of rod lens, the image will be reversed. When the number of rod lens groups in the relay optical system 12 is an odd number, the second intermediate image transferred is an upright real image. When the relay optical system 12 transfers (or inverts) the first intermediate image 1:1 to the image side of the relay optical system 12 to form the second intermediate image, multiple intermediate images can be formed in the relay optical system 12.

The magnifying unit 15 transmits the second intermediate image to the first camera unit 13 and the second camera unit 14, so as to generate magnified images of the target object in the first camera unit 13 and the second camera unit 14 respectively, that is, the first image and the second image. In some embodiments, the second intermediate image may be formed at the focal plane of the object side of the magnifying unit 15, so that the light rays forming the second intermediate image pass through the magnifying unit 15 to form parallel light (i.e., imaging the second intermediate image at infinity), the parallel light can be simultaneously captured by the first camera unit 13 and the second camera unit 14 to generate the first image and the second image respectively. That is to say, the first camera unit 13 and the second camera unit 14 can capture the second intermediate image through the magnifying unit 15 at the same time. Based on the principle of rectilinear propagation of light, what the first camera unit 13 and the second camera unit 14 actually capture is the object plane of the target object, thus the first image and the second image may be respectively generated based on the object plane of the target object.

In some embodiments, the distance between the first camera unit 13 and the second camera unit 14 is less than or equal to 3 mm. In one example, the distance is 3 mm, in another example, the distance is 2 mm, and in yet another example, the distance is 0.5 mm.

Figure 2:
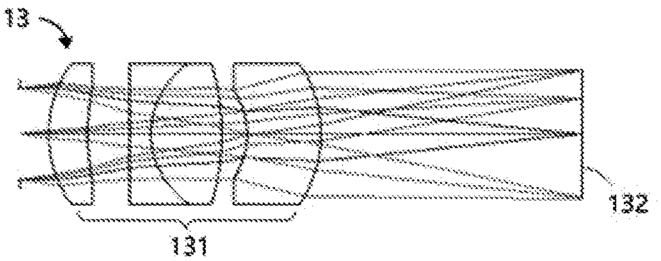
FIG. 2 is a structural schematic diagram of a first camera unit in the embodiment shown in FIG. 1.

Referring to FIG. 2, in some embodiments, the first camera unit 13 includes a first camera lens 131 and a first imaging sensor 132; the magnifying unit 15 and the first camera lens 131 form a first magnification device for forming the first image on the first imaging sensor 132 with the light collected by the objective lens 11 at the distal end of the endoscope transmitted by the relay optical system 12; the first image is a magnified image of the target object.

Figure 3:
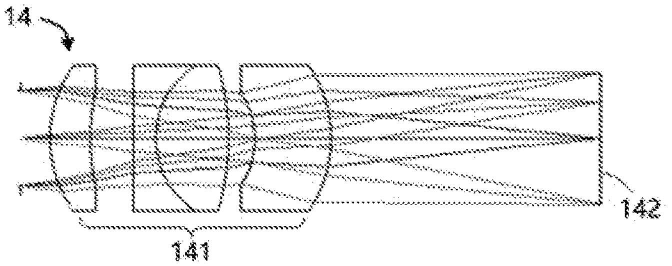
FIG. 3 is a structural schematic diagram of a second camera unit in the embodiment shown in FIG. 1.

Referring to FIG. 3, the second camera unit 14 includes a second camera lens 141 and a second imaging sensor 142; the magnifying unit 15 and the second camera lens 141 form a second magnification device for forming the second image on the second imaging sensor 142 with the light collected by the objective lens 11 at the distal end of the endoscope transmitted by the relay optical system 12; the second image is a magnified image of the target object.

In this embodiment, the magnifying unit 15 and the first imaging lens 131 form a first magnification device, that is, the magnifying unit 15 and the first imaging lens 131 are integrally designed as a first magnification device, and the first magnification device is in the form of a Liszt-like microscope objective, the emergent light of the magnifying unit 15 is parallel light, and the parallel light enters the first camera lens 131 and converges on the first imaging sensor 132 for imaging.

In the same way, the magnifying unit 15 and the second camera lens 141 form the second magnification device, that is, the magnifying unit 15 and the second camera lens 141 are integrally designed as the second magnification device, and the second magnification device is also in the form of a Liszt-like microscope objective, the emergent light of the magnifying unit 15 is parallel light, and the parallel light enters the second camera lens 141 and converges on the second imaging sensor 142 for imaging.

In this embodiment, the magnifying unit 15 and the first camera lens 131 are integrally designed as the first magnification device, and the magnifying unit 15 and the second camera lens 141 are integrally designed as the second magnification device, so that the inherent camera lens of the first camera unit 13 and of the second camera unit 14 may be fully utilized to cooperate with the magnifying unit 15 to achieve the formation of a magnified image of the target object on the first imaging sensor 132 and the second imaging sensor 142, thereby reducing the use of the optical device by the magnifying unit 15 itself, and shortening the length of the magnifying unit 15, so that the length of the endoscope may be shortened as a whole, which not only helps to reduce the manufacturing cost of the endoscope, but also facilitates the use and operation of the endoscope.

In some examples, the first camera lens 131 and the second camera lens 141 may respectively be camera lenses with an imaging resolution of 1080 P. In some other examples, the first camera lens 131 and the second camera lens 141 may respectively be camera lenses with an imaging resolution of 4 K. In yet some examples, the first camera lens 131 and the second camera lens 141 may respectively be camera lenses with an imaging resolution of 8 K.

In some examples, the first imaging sensor 132 and the second imaging sensor 142 may respectively be CCD (Charge-coupled Device). In some other examples, the first imaging sensor 132 and the second imaging sensor 142 may respectively be CMOS (Complementary Metal Oxide Semiconductor).

In some embodiments, the imaging resolution of the first camera lens 131 and the second camera lens 141 may be 4 K, and the sizes of the first imaging sensor 132 and the second imaging sensor 142 may respectively be 1"/1.8, 1"/3, 1"/2.5 or 1"/2.

In some other embodiments, the imaging resolution of the first camera lens 131 and the second camera lens 141 may be 720 P, and the sizes of the first imaging sensor 132 and the second imaging sensor 142 may be 1"/18 or 1"/12.

In some embodiments, the first camera unit 13 and the second camera unit 14 may rotate around the optical axis of the magnifying unit 15 together. In other words, while keeping the first camera unit 13 and the second camera unit 14 stationary, the objective lens 11, the relay optical system 12 and the magnifying unit 15 can be rotated together by an angle around the optical axis of the magnifying unit 15. Wherein, the objective lens 11, the relay optical system 12 and the magnifying unit 15 are also designed in an integrated manner, and the three may be connected together physically and their relative positions are fixed.

When the objective lens 11 has a field angle (such as a field angle of 30 degrees, 45 degrees, 50 degrees, or 70 degrees) that can obliquely view the target object, the field of view of the objective lens 11 can be changed by rotating the integrated structure of the objective lens 11, the relay optical system 12 and the magnifying unit 15 around the optical axis of the magnifying unit 15 (i.e., the optical axis of the relay optical system 12).

In this case, since the first camera unit 13 and the second camera unit 14 are kept stationary, the plane where the optical axis of the first camera unit 13 and the optical axis of the second camera unit 14 are located is always kept in the horizontal direction, so the orientation of the target image captured by the first camera unit 13 and the second camera unit 14 may be kept unchanged (such as always in the upright direction), so that the observer may observe the image that is in the upright direction all the time, avoiding to rotate the objective lens 11, the relay optical system 12 and the magnifying unit 15 around the optical axis of the magnifying unit 15 in order to obtain a different field of view, which will cause the obtained image to rotate accordingly, or even cause the problem of not being able to image.

The magnifying unit 15 can magnify the exit angle of light passing through the magnifying unit 15, so that at a relatively small exit pupil distance, the light spot required by the clear apertures of the first camera unit 13 and the second camera unit 14 can be obtained.

In some embodiments, the exit angle of light of the magnifying unit 15 is greater than 15°. In some embodiments, the exit angle of light of the magnifying unit 15 may range from 15° to 70°. In one example, the exit angle of light of the magnifying unit 15 is 15°, 20° or 25°; in another example, the exit angle of light of the magnifying unit 15 is 30°; in yet another example, the exit angle of light of the magnifying unit 15 is 35°; in still another example, the exit angle of light of the magnifying unit 15 is 40°.

The exit pupil distance is the axial distance between the lens closest to the image side in the magnifying unit 15 and the lens closest to the object side in the first camera unit 13 or the second camera unit 14.

In some embodiments, the exit pupil distance of the magnifying unit 15 is greater than 5 mm. In some embodiments, the exit pupil distance of the magnifying unit 15 may range from 5 mm to 50 mm. In one example, the exit pupil distance of the magnifying unit 15 is 5 mm, 10 mm, 15 mm or 20 mm; in another example, the exit pupil distance of the magnifying unit 15 is 25 mm; in yet another example, the exit pupil distance of the magnifying unit 15 is 30 mm; in still another example, the exit pupil distance of the magnifying unit 15 is 40 mm.

In one example, the exit pupil distance of the magnifying unit 15 is more than 30 mm, and the spot size is 26 mm, which are capable of meeting the requirements for the clear apertures of two sets of 4 K camera lenses.

In some embodiments, the exit pupil distance of the magnifying unit 15 is adjustable, and the adjustable range may be ±2 mm, which is used to compensate system processing errors and assembly errors.

Figure 4:
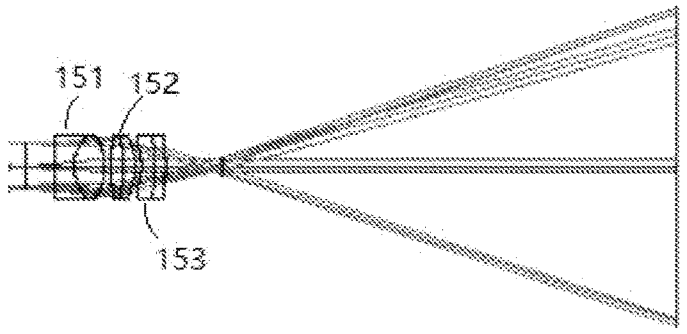
FIG. 4 is a structural schematic diagram of a magnifying unit in the embodiment shown in FIG. 1.

In order to obtain a larger exit angle, in some embodiments, the overall focal power of the magnifying unit 15 is negative. Referring to FIG. 4, in an embodiment, the magnifying unit 15 includes a first magnifying unit 151, a second magnifying unit 152 and a third magnifying unit 153. Wherein, the first magnifying unit 151, the second magnifying unit 152 and the third magnifying unit 153 are all cemented doublets and have a Liszt-like structure.

The first magnifying unit 151, includes a first lens with negative focal power and a second lens with positive focal power. The image side of the first lens and the object side of the second lens are cemented to each other to form a first cemented lens. Wherein, the object side of the first lens is concave, and the image side of the first lens is concave; the object side of the second lens is convex, and the image side of the second lens is convex.

In some examples, the ratio of the focal length to the effective apertures on the object side of the first lens is preferably (−3.40, −2.95), and the refractive index of the first lens is preferably greater than 1.7. The ratio of the focal length to the effective apertures on the object side of the second lens is preferably (2.95, 2.70), and the refractive index of the second lens is preferably greater than 1.6.

In some embodiments, the Abbe numbers of the first lens and the second lens meet the following requirements:

$$vd2-vd1>15;$$

Wherein, vd1 is the dispersion coefficient of the first lens at line d, and vd2 is the dispersion coefficient of the second lens at line d.

Through the ratio of the focal length to the effective apertures of the object side of the first lens and the second lens, as well as the above-mentioned collocation of refractive index and Abbe number (also known as the dispersion system, it is used to represent the index of the dispersion ability of the transparent medium, the smaller the value, the more serious the dispersion phenomenon), the increase of edge aberrations (coma, lateral chromatic aberration, astigmatism and field curvature) caused by the increase of the field of view of the system can be greatly reduced, which helps to avoid tailing and edge blurring and other issues, and generate high-quality images with chromatic aberration restoration and solid imaging focus.

The second magnifying unit 152 includes a third lens with positive focal power and a fourth lens with negative focal power, the image side of the third lens and the object side of the fourth lens are cemented to each other to form a second cemented lens. Wherein, the object side of the third lens is convex, and the image side of the third lens is convex; the object side of the fourth lens is concave, and the image side is convex.

In some examples, the ratio of the focal length to the effective apertures on the object side of the third lens is preferably (2.76, 2.93), and the refractive index of the third lens is preferably greater than 1.6; the ratio of the focal length to the effective apertures on the object side of the fourth lens is preferably (−3.15, −2.78), and the refractive index of the fourth lens is preferably greater than 1.5.

In some embodiments, the Abbe numbers of the third lens and the fourth lens meet the following requirements:

$$vd3-vd4>20;$$

Wherein, vd3 is the dispersion coefficient of the third lens at the line d, and vd4 is the dispersion coefficient of the fourth lens at the line d.

Through the ratio of the focal length to the effective apertures on the object side of the third lens and the fourth lens, as well as the above-mentioned collocation of refractive index and Abbe number, the increase of edge aberration caused by the increase of the field of view of the system can be greatly reduced, which helps to avoid problems such as tailing and edge blurring, and generate high-quality images with chromatic aberration restoration and solid imaging focus.

The third magnifying unit 153 includes a fifth lens with negative focal power and a sixth lens with negative focal power; the image side of the fifth lens and the object side of the sixth lens are cemented to each other to form a third cemented lens. Wherein, the object side of the fifth lens is concave, and the image side of the fifth lens is convex; the object side of the sixth lens is concave, and the image side of the sixth lens is convex.

In some examples, the ratio of the focal length to the effective apertures on the object side of the fifth lens is preferably (−2.10, −1.94), and the refractive index of the fifth lens is preferably greater than 1.5; the ratio of the focal length to the effective apertures on the object side of the sixth lens is preferably (−3.91, −2.88), and the refractive index of the sixth lens is preferably greater than 1.6.

In some embodiments, the Abbe numbers of the fifth lens and the sixth lens meet the following requirements:

$$vd6-vd5>10;$$

Wherein, vd5 is the dispersion coefficient of the fifth lens at line d, and vd6 is the dispersion coefficient of the sixth lens at line d.

Through the ratio of the focal length of the fifth lens and the sixth lens to the effective apertures on the object side, as well as the above-mentioned collocation of refractive index and Abbe number, the increase of edge aberrations (coma, lateral chromatic aberration, astigmatism and field curvature) caused by the increase of the field of view of the system may be greatly reduced, which helps to avoid tailing and edge blurring and other issues, and generate high-quality images with chromatic aberration restoration and solid imaging focus.

Figure 5:
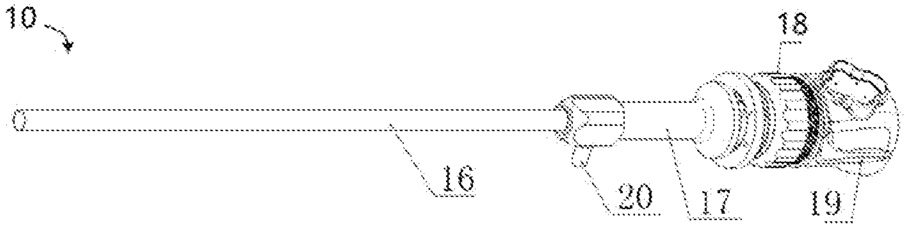
FIG. 5 is a three-dimensional structural schematic diagram of an embodiment of a rotatable 3D endoscope with integrated design of the optical system and the camera unit of the present application.

Referring to FIG. 5, in some embodiments, the rotatable 3D endoscope 10 may further include: an insertion tube 16, a magnifying unit support 17, a camera unit support 18 and a handle 19.

The objective lens 11 and the relay optical system 12 in the embodiment shown in FIG. 1 are disposed in the insertion tube 16, wherein the objective lens 11 is disposed at the distal end of the insertion tube 16. The rotation of the objective lens 11, the relay optical system 12 and the magnifying unit 15 can be realized by rotating the insertion tube 16.

The first end of the magnifying unit support 17 is connected to the proximal end of the insertion tube 16, and the magnifying unit 15 shown in FIG. 1 is disposed in the magnifying unit support 17.

The first end of the camera unit support 18 is connected to the second end of the magnifying unit support 17; the first camera unit 13 and the second camera unit 14 in the embodiment shown in FIG. 1 are disposed side by side on the camera unit support 18.

The handle 19 is connected to the second end of the camera unit support 18.

In some embodiments, the camera unit support 18 is rotatable around the optical axis of the magnifying unit 15. In other words, the insertion tube 16 can be rotated around the optical axis of the magnifying unit 15 by an angle while keeping the camera unit support 18 stationary, and the field of view of the objective lens 11 can be changed.

In this case, since the camera unit support 18 is kept stationary, that is, the first camera unit 13 and the second camera unit 14 are kept stationary, such as keeping the plane where the optical axis of the first camera unit 13 and the optical axis of the second camera unit 14 are located always in the horizontal direction, so that the orientation of the target image captured by the first camera unit 13 and the second camera unit 14 may be kept unchanged (such as always in the upright direction), so that the observer may observe the image that is in the upright direction all the time, avoiding to rotate the insertion 16 around the optical axis of the magnifying unit 15 in order to obtain a different field of view, which will cause the obtained image to rotate accordingly, or even cause the problem of not being able to image.

Figure 6:
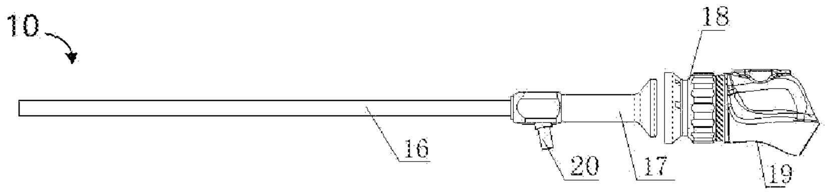
FIG. 6 is a schematic diagram of the separation of the camera unit support and the magnifying unit in FIG. 5.

Referring to FIG. 6, in some embodiments, the first end of the camera unit support 18 is detachably connected to the second end of the magnifying unit support 17.

In one example, the end portion of the second end of the magnifying unit support 17 has a locking connection protrusion for clipping into the first end of the camera unit support 18; the first end of the camera unit support 18 has a bayonet for accommodating the locking connection protrusion, the edge of the bayonet is provided with an elastic locking connection member (not shown in the figure). When the first end of the camera unit support 18 is connected to the second end of the magnifying unit support 17, the locking connection protrusion is inserted into the bayonet, and the elastic locking connection member clips the locking connection protrusion into the bayonet.

In one example, the elastic locking connection member may include a locking piece and a restoring elastic member. The side wall of the bayonet has a notch for installing the locking piece. The locking piece includes a pressing part, a hinge connection part and a locking connection part, and the hinge connection part is located between the pressing part and the locking connection part. The locking piece is disposed in the notch, hinged at the bayonet through the hinge connection part, and connected with the restoring elastic member (such as a torsion spring). In a natural state, the pressing part protrudes from the notch, and the locking connection part extends into the bayonet. When the pressing part is pressed, the pressing part moves downward, and the locking connection part is retracted from the inside of the bayonet through leverage. When the pressing part is released, the pressing part moves to the outside of the notch under the action of the restoring elastic member, and the locking connection part is extended into the inside of the bayonet through leverage.

Figure 7:
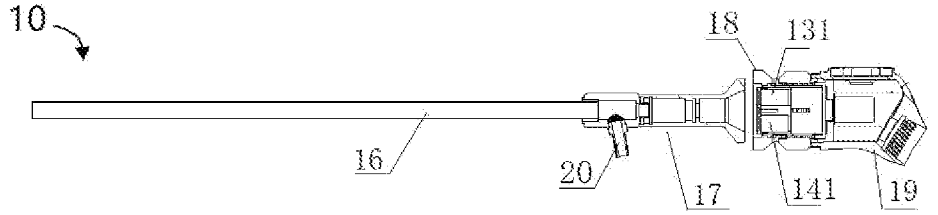
FIG. 7 is a partial sectional view of FIG. 6.
Figure 8:
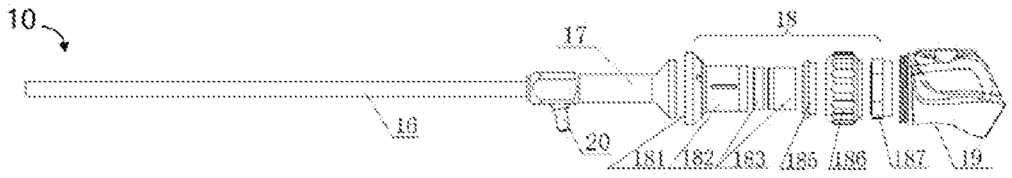
FIG. 8 is an exploded view of the endoscope shown in FIG. 5.

Referring to FIG. 7 and FIG. 8, in one embodiment, the camera unit support 18 may include an endoscope bayonet 181, a focusing catheter 182, a lens group cover 183, a connecting seat 185, a focusing handwheel 186 and a sensor support 187. The endoscope bayonet 181 is connected to the focusing catheter 182, for example, may be fixedly connected by screws. The lens group cover 183 is disposed in the focusing catheter 182 for supporting the first camera lens 131 and the second camera lens 141. The sensor support 187 is disposed at one end of the lens group cover 183 for supporting the first imaging sensor 132 and the second imaging sensor 142.

The tail end of the focusing catheter 182 is connected to the handle 19 through the connection seat 183, for example, the focusing catheter 182 and the handle 19 may be threadedly connected to both ends of the connecting seat 183 respectively. When the tail end of the focusing catheter 182 is connected with the handle 19, the sensor support 187 is located within the cavity of the handle 19. The first imaging sensor 132 and the second imaging sensor on the sensor support 187 may be connected to an external image processing device through a data line.

In some examples, the lens group cover 183 includes a first lens group fixing seat and a second lens group fixing seat, and the first lens group fixing seat and the second lens group fixing seat are fixedly connected by screws.

Figure 9:
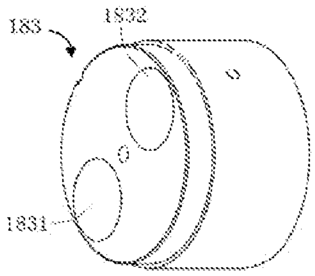
FIG. 9 is a three-dimensional structural schematic diagram of the lens group cover in an embodiment of the present application.

Referring to FIG. 9, in one example, the lens group cover 183 includes a first fixing hole 1831 and a second fixing hole 1832, the first camera lens 131 is disposed in the first fixing hole 1831, and the second camera lens 141 is disposed in the second fixing hole 1832.

The focusing handwheel 186 is sleeved on the focusing catheter 182. The focusing handwheel 186 is provided with teeth; the focusing catheter is provided with a slot; the first end of the guide column (not shown in the figure) is connected to the lens group cover 183 through the slot, and the second end of the guide column is connected to the teeth of the focusing catheter 182. The teeth match each other, so that when the focusing handwheel 186 is rotated, the focusing handwheel 186 can drive the guide column to move together, and the rotation of the guide column can be restricted through the slot hole, so that the guide column can only move horizontally, thereby driving the lens group cover 183 to move along the axis of the focusing catheter 182. Rotating the focusing handwheel 186 clockwise may drive the lens group cover 183 to move forward along the axis of the focusing catheter 182, and rotating the focusing handwheel 186 counterclockwise may drive the lens group cover 183 to move backward along the axis of the focusing catheter 182.

In order to provide illumination to the objective lens 11 at the distal end of the endoscope insertion tube 16, in some embodiments, an optical fiber for illumination is provided in the insertion tube 16.

In one example, an optical fiber mount 20 may be provided on the insertion tube 16, and the optical fiber mount 20 may be provided with a through-hole. The insertion tube 16 is provided with an optic fiber hole connected to the through-hole on the optical fiber mount 20, and an optical fiber for illumination may be threaded through the through-hole and the optic fiber hole. The optical fiber mount 20 may be disposed at a position where the insertion tube 16 is connected with the magnifying unit 15.

In the above embodiments, the first end of the camera unit support 18 is detachably connected to the second end of the magnifying unit support 17. The present application is not limited thereto. In other embodiments, the first end of the camera unit support 18 and the second end of the magnifying unit support 17 may also be fixedly connected.

In some embodiments, the first camera unit 13 and the second camera unit 14 can capture the third intermediate image through the magnifying unit 15 at the same time. Based on the principle of rectilinear propagation of light, what the first camera unit 13 and the second camera unit 14 actually capture is the object plane of the target object, thus the first image and the second image can be respectively generated based on the object plane of the target object. The third intermediate image is an image generated at the imaging plane on the image side of the magnifying unit 15 after the magnifying unit 15 magnifies the second intermediate image, and the third intermediate image is a magnified image of the second intermediate image.

Embodiment 2

Figure 10:
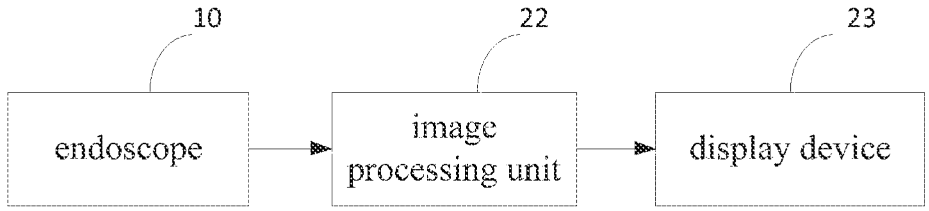
FIG. 10 is a schematic diagram of modules of an embodiment of the endoscope imaging system of the present application.

Referring to FIG. 10, an embodiment of the present application provides an endoscope imaging system, including: an endoscope 10, an image processing unit 22 and a display device 23. Wherein, the endoscope 10 is the endoscope described in any one of the first embodiment.

The endoscope 10 is used for obtaining light reflected by a target object to be observed, and simultaneously generate a first image and a second image of the target object based on the light.

The image processing unit 22 is electrically connected to the endoscope 10 and is used for generating a 3D image of the target object based on the first image and the second image.

The display device 23 is electrically connected with the image processing unit 22 and is used for displaying the 3D image.

In some embodiments, since the optical centers of the first camera unit and the second camera unit in the endoscope 10 are on a straight line, the distance between the two optical centers is the interpupillary distance of the stereo vision system. Due to the interpupillary distance, the imaging of the object by the first and second camera units through the objective lens, the relay optical system and the magnifying unit forms a visual difference to obtain the first image and the second image respectively. The first image and the second image are processed by the image processing unit 22 to finally form a 3D visual effect with depth information.

The implementation principles and technical effects of the endoscope imaging system provided in this embodiment are basically the same as those of any of the aforementioned 3D endoscope embodiments, and will not be repeated here.

Embodiment 3

Figure 11:
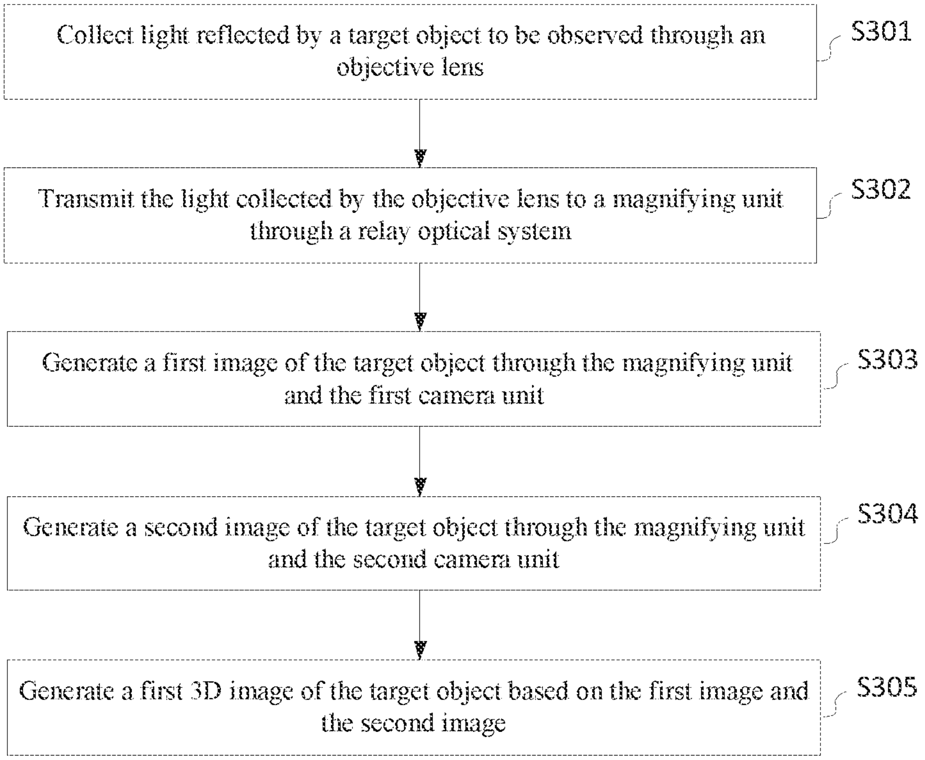
FIG. 11 is a schematic flowchart of an embodiment of an endoscope 3D imaging method of the present application.

Referring to FIG. 11, an embodiment of the present application provides an endoscope 3D imaging method, including:

S301. Collect light reflected by a target object to be observed through an objective lens.

S302. Transmit the light collected by the objective lens to a magnifying unit through a relay optical system.

S303. Generate a first image of the target object through the magnifying unit and the first camera unit.

S304. Generate a second image of the target object through the magnifying unit and the second camera unit.

S305. Generate a first 3D image of the target object based on the first image and the second image.

The endoscope 3D imaging method provided in this embodiment are basically the same as the 3D imaging process and technical effect in any of the foregoing 3D endoscope embodiments, and will not be repeated here.

In some embodiments, the generating the first image of the target object through the magnifying unit and the first camera unit (step S303) includes: using the magnifying unit and the camera lens 131 of the first camera unit to magnify the light spot on the image side of the relay optical system, and form the first image on the first imaging sensor 132 in the first camera unit; the first image is a magnified image of the target object.

The generating the second image of the target object through the magnifying unit and the second camera unit (step S304) includes: using the magnifying unit and the second camera lens of the second camera unit to magnify the light spot on the image side of the relay optical system, and form the second image on the second imaging sensor in the second camera unit; the second image is a magnified image of the target object.

In this embodiment, the magnifying unit is integrated with the first imaging lens 131, and the magnifying unit is integrated with the second imaging lens to respectively realize the magnification of the light spot on the image side of the relay optical system, which can make full use of the inherent camera lenses of the first camera unit and the second camera unit, to cooperate with the magnifying unit to realize the magnified image of the target object on the first imaging sensor and the second imaging sensor, thereby reducing the use of the optical device by the magnifying unit itself, and shortening the length of the magnifying unit 15, so that the length of the endoscope may be shortened as a whole, which not only helps to reduce the manufacturing cost of the endoscope, but also facilitates the use and operation of the endoscope.

In some embodiments, after generating the first 3D image of the target object (step S305), the endoscope 3D imaging method further includes the steps of: keeping the first camera unit and the second camera unit stationary, rotating the objective lens, the relay optical system and the magnifying unit by an angle around the optical axis of the magnifying unit; generating a third image of the target object through the magnifying unit and the first camera unit; generating a fourth image of the target object by the magnifying unit and the second camera unit; generating a second 3D image of the target object based on the third image and the fourth image; wherein, the image content of the second 3D image has the same spatial orientation as the image content of the first 3D image.

In this embodiment, when the objective lens, the relay optical system, and the magnifying unit are rotated by an angle around the optical axis of the magnifying unit to change the field of view, since the first imaging unit and the second camera unit keep stationary, such as keeping the plane where the optical axis of the first camera unit and the optical axis of the second camera unit are located always in the horizontal direction, so that the orientation of the target image obtained by the first camera unit and the second camera unit may be kept unchanged (such as always in the upright direction), so that the observer may observe the image that is in the upright direction all the time, avoiding to rotate the objective lens, the relay optical system and the magnifying unit in order to obtain a different field of view, which will cause the obtained image to rotate accordingly, or even cause the problem of not being able to image.

Embodiment 4

The present embodiment provides a 3D camera device with a simple structure.

Embodiment of the 3D camera device of the present application will be described in detail below in conjunction with FIG. 12 to FIG. 18.

Figure 12:
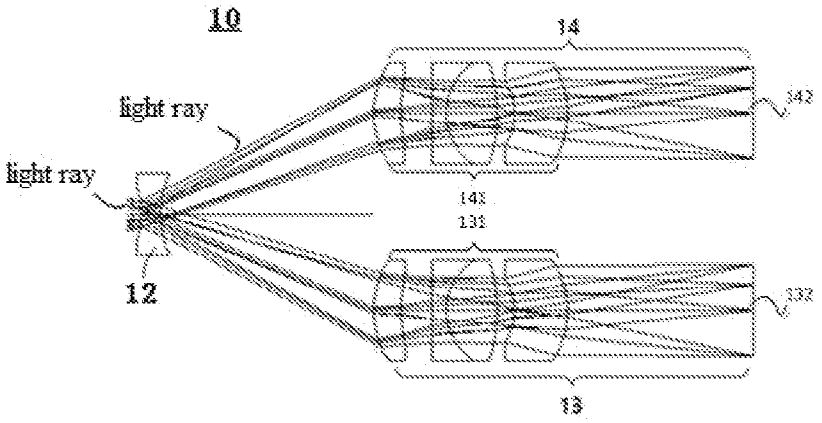
FIG. 12 is a structural schematic diagram of the first embodiment of the 3D camera device of the present application.

FIG. 12 shows a structural schematic diagram of the first embodiment of the 3D camera device of the present application. For clarity, FIG. 12 shows only the optical system of the 3D camera device. Referring to FIG. 12, the 3D camera device 10 of the present embodiment, includes: a concave lens 12, a first camera unit 13 and a second camera unit 14; the concave lens 12, is used to magnify the exit angle of the light reflected by the target to be imaged after passing through the concave lens; the first camera unit 13 and the second camera unit 14 are disposed on the image side of the concave lens 12, and the clear apertures of the first camera unit 13 and the second camera unit 14 are located within the spot range of the emergent light of the concave lens 12.

Figure 13:
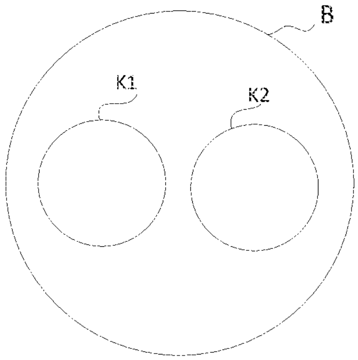
FIG. 13 is a schematic diagram between the spot of the concave lens and the clear apertures of the camera unit in an embodiment of the 3D camera device of the present application.

FIG. 13 is a schematic diagram between the light spot of the concave lens and the clear apertures of the camera unit; wherein B represents the spot range of the emergent light of the concave lens, K1 represents the clear aperture of the first camera unit 13, and K2 represents the clear aperture of the second camera unit 14.

The first camera unit 13 and the second camera unit 14 are disposed on the image side of the concave lens 12, and the clear apertures of the first camera unit 13 and the second camera unit 14 are located within the spot range of the emergent light of the concave lens 12, while the first camera unit and the second camera unit each have a certain field angle (such as 20 degrees-120 degrees), and the light spot of the emergent light of the concave lens 12 is located within the field angle range of the first camera unit 13 and the second camera unit 14, so that the light reflected by the target can enter the first camera unit and the second camera unit through the same concave lens, that is, the first camera unit and the second camera unit can simultaneously shoot the image of the target through the same concave lens. Due to the different positions of the first camera unit and the second camera unit relative to the concave lens, the images of the target shot simultaneously by the first camera unit and the second camera unit through the same concave lens have a certain parallax, thereby facilitating the subsequent generation of the 3D image of the target according to the image with parallax of the target obtained by the first camera unit and the second camera unit. Compared with the 3D camera device where the two camera units each realize 3D imaging through an optical light-guide structure, in the embodiment of the present application, the two camera units can shoot images of the same target with parallax through the same concave lens, and the structure is simpler.

The first camera unit captures the first image of the target through the concave lens, and the second camera unit simultaneously captures the second image of the target through the same concave lens. Due to the different positions of the first camera unit and the second camera unit relative to the concave lens, the first image and the second image have a certain parallax, and subsequently a 3D image of the target can be generated based on the first and second images with parallax according to existing techniques.

The concave lens 12 may be a single-sided concave lens, that is, the optical surface of the image side (i.e., the side close to the first camera unit 13 and the second camera unit 14) of the concave lens is concave, or the optical surface of the object side (i.e., the side close to the target to be imaged) of the concave lens is concave.

The concave lens may also be a double-sided concave lens, that is, the optical surface of the side close to the first camera unit 13 and the second camera unit 14 of the concave lens is concave, and the optical surface of the side close to the target to be imaged of the concave lens is concave.

The exit angle of light of the concave lens is 15° or more. In some embodiments, the range of the exit angle of light of the concave lens may be 15°~40°. In one example, the concave lens has an exit angle of light of 15°, 20°, or 25°; in another example, the concave lens has an exit angle of light of 30°; in yet another example, the concave lens has an exit angle of light of 35°; and in still another example, the concave lens has an exit angle of light of 40°.

Referring to FIG. 12, the axial distance between the first camera unit 13 and the second camera unit 14 and the concave lens is large, and the diameter size of the concave lens may be relatively small, facilitating processing and production. The diameter size of the concave lens may be less than the sum of the diameter of the lens of the first camera unit 13 and the diameter of the lens of the second camera unit 14.

In some embodiments, the axial distance between the first camera unit 13 and the second camera unit 14 and the concave lens is adjustable, so that the first camera unit 13 and the second camera unit 14 can obtain a clear image of the observation target through the concave lens.

The concave lens and the first camera unit 13 and the second camera unit 14 may be jointly disposed in a cylindrical housing. Operating the concave lens can cause the concave lens to move towards or away from the first camera unit 13 and the second camera unit 14 in the housing to adjust the distance between the concave lens and the first camera unit 13 and the second camera unit 14; the first camera unit 13 and the second camera unit 14 may also be operated so that the first camera unit 13 and the second camera unit 14 move towards or away from the concave lens in the housing to adjust the distance between the first camera unit 13 and the second camera unit 14 and the concave lens.

The concave lens 12 in the present embodiment is a single concave lens, and in other embodiments, the concave lens 12 may also be composed of a plurality of concave lenses.

The first camera unit 13 includes a lens 131 and an imaging sensor 132. The second camera unit 14 includes a lens 141 and an imaging sensor 142. The imaging sensor can be CCD (Charge-coupled Device) or CMOS (Complementary Metal Oxide Semiconductor). In some examples, the size of the CMOS sensor of the first camera unit or the second camera unit is ⅓ inch, ⅙ inch, 1/10 inch, 1/11 inch or 1/18 inch.

The first camera unit 13 and the second camera unit 14 are both camera units with an imaging resolution of 4 K. In other embodiments, the first camera unit 13 and the second camera unit 14 are also both camera units with an imaging resolution of 1080 P.

In some embodiments, the first camera unit 13 and the second camera unit 14, may rotate together around the optical axis of the concave lens 12. In other words, while keeping the first camera unit 13 and the second camera unit 14 stationary, the concave lens 12 may be rotated by an angle around its own optical axis.

In this case, since the first camera unit 13 and the second camera unit 14 are kept stationary, such as keeping the plane where the optical axis of the first camera unit 13 and the optical axis of the second camera unit 14 are located always in the horizontal direction, so that the orientation of the target image captured by the first camera unit 13 and the second camera unit 14 remains unchanged (such as always in the upright direction), so that the observer can observe the image that is in the upright direction all the time, avoiding to rotate the concave lens 12 around the optical axis of the concave lens, which will cause the obtained image to rotate accordingly, or even cause the problem of not being able to image.

Figure 14:
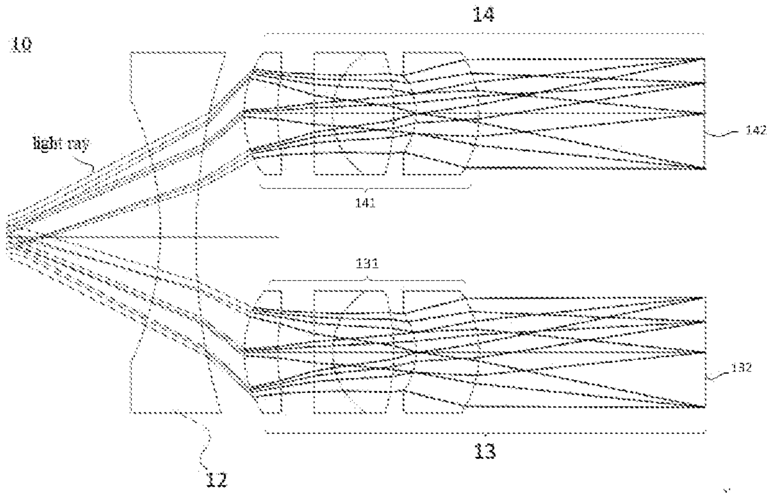
FIG. 14 is a structural schematic diagram of the second embodiment of the 3D camera device of the present application.

FIG. 14 shows a structural schematic diagram of the second embodiment of the 3D camera device of the present application. The present embodiment is substantially the same as the embodiment shown in FIG. 12, except that, in the present embodiment, the concave lens 12 is disposed closer to the first camera unit 13 and the second camera unit 14.

In some embodiments, the distances between the center of the concave lens 12 and the first camera unit 13 and the second camera unit 14 along the optical axis direction of the concave lens are 1-10 mm respectively.

The diameter of the concave lens 12 may be greater than the sum of the diameter of the lens of the first camera unit 13 and the diameter of the lens of the second camera unit 14. The first camera unit 13 and the second camera unit 14 are disposed side by side and adjacent to each other and correspond to the light exit face of the concave lens.

In one example, the concave lens 12 has a diameter of 10 mm, the diameter of the lens of the first camera unit 13 and the lens of the second camera unit 14 are 4 mm respectively.

Figure 15:
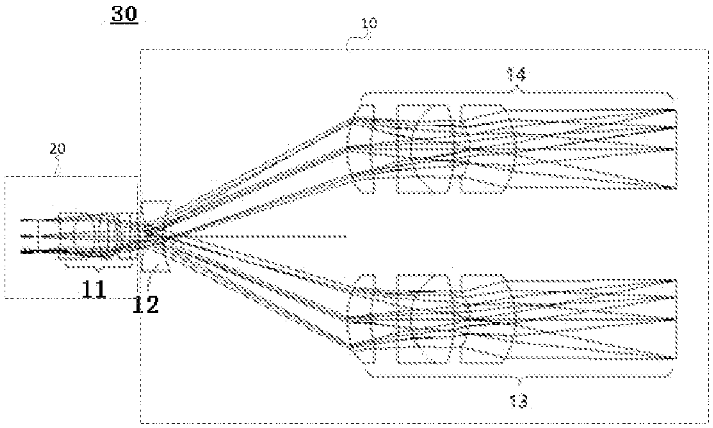
FIG. 15 is a structural schematic diagram of the first embodiment of the 3D endoscope of the present application.

An embodiment of the present application also provides a 3D optical endoscope. FIG. 15 shows a structural schematic diagram of the first embodiment of the 3D endoscope of the present application. Referring to FIG. 15, the 3D optical endoscope 30 of the present embodiment may include: a 2D optical endoscopic imaging unit 20 and a 3D camera device 10; the central axis of the 3D camera device 10 is coaxial with the central axis of the 2D optical endoscopic imaging unit 20; the 3D camera device 10, disposed on the image side of the 2D optical endoscopic imaging unit, for forming a first image and a second image of the observation target located on the object side of the 2D optical endoscopic imaging unit 20 from different angles of view through the 2D optical endoscopic imaging unit.

Wherein the 2D optical endoscopic imaging unit 20 can be inserted at least partially into the patient's body, and the 3D camera device is located outside the patient's body.

The 3D camera device is the 3D camera device 10 described in any of the aforementioned embodiments. The exit angle of light of the 2D optical endoscopic imaging unit 20 is magnified by the concave lens 12 so that the clear apertures of the first camera unit 13 and the second camera unit 14 disposed on the image side of the concave lens 12 are capable of locating within the spot range of the emergent light of the concave lens 12, and the first camera unit 13 and the second camera unit 14 each have a certain field angle (such as 20 degrees-120 degrees), the light spot of the emergent light of the concave lens 12 is located within the field angle range of the first camera unit 13 and the second camera unit 14, so that the light reflected by the target can enter the first camera unit and the second camera unit through the same concave lens, that is, the first camera unit and the second camera unit can simultaneously shoot the image of the target through the same concave lens. Due to the different positions of the first camera unit and the second camera unit relative to the concave lens, the images of the target shot simultaneously by the first camera unit and the second camera unit through the same concave lens have a certain parallax, thereby facilitating the subsequent generation of the 3D image of the target using existing technology according to the image with parallax of the target obtained by the first camera unit and the second camera unit. Compared with the 3D camera device where the two camera units each realize 3D imaging through an optical light-guide structure, in the embodiment of the present application, the two camera units can shoot images of the same target with parallax through the same concave lens, and the structure is simpler.

The central axis of the 3D camera device is coaxial with the optical axis of the concave lens in the 3D camera device. The central axis of the 2D optical endoscopic imaging unit is coaxial with the optical axis of the 2D optical endoscopic imaging unit.

The structure and function of the 3D camera device in the present embodiment is substantially the same as the structure and function of the 3D camera device in the aforementioned embodiment.

In some embodiments, the 2D optical endoscopic imaging unit, can be used to form a light spot capable of forming a real image of the observation target on the image side of the 2D optical endoscopic imaging unit. The light that forms the light spot of the real image can enter the first camera unit and the second camera unit to form the first image and the second image of the observation target respectively.

In other words, the first camera unit and the second camera unit can shoot the light spot forming the real image, since the light spot is formed after the light of the observation target passes through the 2D optical endoscopic imaging unit, based on the linear propagation of light, the first camera unit and the second camera unit are actually able to shoot the observation target through the 2D optical endoscopic imaging unit, thereby obtaining the first image and the second image of the observation target.

The 3D camera device in the present embodiment can be used in conjunction with various forms of 2D optical endoscopic imaging units. For example, the 2D optical endoscopic imaging unit may be at least one 2D optical endoscopic imaging unit with a cross-sectional diameter of 2.7 mm, 3 mm, 4 mm, 5 mm, 8 mm, 10 mm or 12 mm. The cross-sectional diameter of the 2D optical endoscopic imaging unit may be the outer diameter of the anterior tube (also called an insertion tube) of the 2D optical endoscopic imaging unit. The anterior tube may be a tube segment that is at least partially able to be inserted into the patient's body.

In some embodiments, the 3D endoscope includes a cylindrical connector, the first end of the connector is connected to the end of the image side of the endoscopic imaging unit, and the second end of the connector is connected to the end of the object side of the 3D camera device.

In some embodiments, the axial distance between the 3D camera device and the endoscopic imaging unit is adjustable.

In some embodiments, the 2D optical endoscopic imaging unit is capable of rotating around the central axis of the 3D camera device. When the 3D camera device is held by hand and kept stationary (such as keeping the plane where the optical axis of the first camera unit 13 and the optical axis of the second camera unit 14 are located always in the horizontal direction), the 2D optical endoscopic imaging unit is rotated around the central axis of the 3D camera device (i.e., the central axis of the 2D optical endoscopic imaging unit itself) by any angle, so that the orientation of the target image captured by the first camera unit 13 and the second camera unit 14 remains unchanged (such as always in the upright direction), so that the observer can observe the image that is in the upright direction all the time, avoiding to rotate the concave lens around the central axis of the concave lens, which will cause the obtained image to rotate accordingly, or even cause the problem that the clear aperture of the first camera unit 13 or the second camera unit 14 is obstructed by certain structural components and is not able to image.

In some embodiments, in the 3D camera device, the concave lens 12 may rotate along the optical axis of the concave lens 12 relative to the first camera unit 13 and the second camera unit 14. The 2D optical endoscopic imaging unit may rotate with the concave lens 12 around the optical axis of the concave lens 12. Thus, when the first camera unit 13 and the second camera unit 14 are held by the hand and kept stationary, the 2D optical endoscopic imaging unit and the concave lens 12 rotate together around the optical axis of the concave lens 12 by any angle relative to the first camera unit 13 and the second camera unit 14, and the orientation of the target image captured by the first camera unit 13 and the second camera unit 14 remains unchanged (such as always in the upright direction), so that the observer can observe the image that is always in the upright direction.

In some embodiments, the endoscopic imaging unit includes a lens or lens group for forming a real image of the observation target.

Referring to FIG. 15, in the 3D endoscope 30, the 2D optical endoscopic imaging unit includes a lens or lens group 11 for forming a real image of the observation target. The lens or lens group 11 may be referred to as an eye lens. The 3D endoscope in the present embodiment is formed by combining the 3D camera device shown in FIG. 12 with a 2D optical endoscope imaging unit with a lens or lens group 11.

Figure 16:
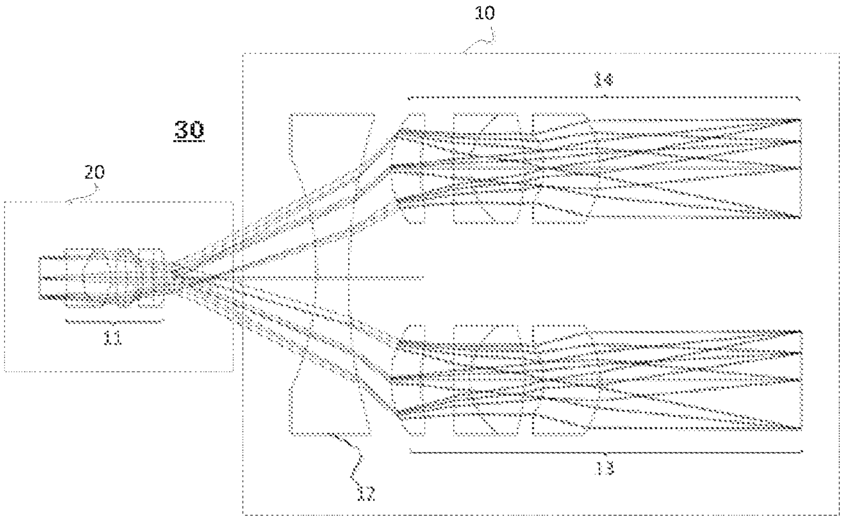
FIG. 16 is a structural schematic diagram of the second embodiment of the 3D endoscope of the present application.

FIG. 16 shows a structural schematic diagram of the second embodiment of the 3D endoscope of the present application. Referring to FIG. 16, in the 3D endoscope 30, the 2D optical endoscopic imaging unit includes a lens or lens group 11 for forming a real image of the observation target. The lens or lens group 11 may be referred to as an eye lens. The 3D endoscope in the present embodiment is formed by combining the 3D camera device shown in FIG. 14 with a 2D optical endoscope imaging unit with a lens or lens group 11.

Figure 17:
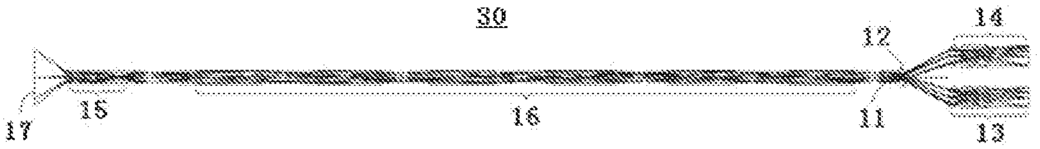
FIG. 17 is a structural schematic diagram of the third embodiment of the 3D endoscope of the present application.

FIG. 17 shows a structural schematic diagram of the third embodiment of the 3D endoscope of the present application. Referring to FIG. 17, the present embodiment is substantially the same as the embodiment shown in FIG. 15, except that, in the present embodiment, the 3D endoscope further includes a relay optical system 16 disposed on the side of the lens or lens group (eye lens) 11, and an objective lens 15 disposed on the object side of the relay optical system 16.

Wherein, the objective lens 15, disposed at the distal end of the endoscope, is used for collecting the light reflected by the target object to be observed outside the distal end of the endoscope; The distal end of the endoscope is the end of the endoscope close to the target object to be observed. The target object to be observed can be lesions in the bladder, nasal cavity and stomach.

The relay optical system 16, disposed on the image side of the objective lens 15, is used for transmitting the light collected by the objective lens 15 at the distal end of the endoscope to the eye lens 11. In other words, the objective lens 15 is disposed on the object side of the relay optical system 16 and can converge the light reflected by the target object to be observed to the relay optical system 16. Wherein, the object side of the relay optical system 16 is the side of the relay optical system 16 close to the target object to be observed.

The relay optical system 16 may be composed of multiple or multiple groups of rod lens, such as three or five groups of odd groups of rod lens. The number of rod lens groups depends on the length of the distance transmitted (working length of the endoscope). The longer the transmission distance, the more rod lens groups are needed, and vice versa.

The objective lens 15 and the relay optical system 16 are disposed at the front end of the endoscope (i.e., the insertion end). In some embodiments, the outer diameter of the endoscope front end may be 3 mm-6 mm.

In some embodiments, the distance between the first camera unit 13 and the second camera unit 14 is less than or equal to 3 mm. In one example, the distance is 3 mm, in another example, the distance is 2 mm, and in yet another example, the distance is 0.5 mm.

When the objective lens 15 has a field angle (such as a field angle of 30 degrees, 45 degrees, 50 degrees, or 70 degrees) that may obliquely view the target object, the field of view of the objective lens 15 may be changed by rotating the objective lens 15 and the relay optical system 16 around the optical axis of the eye lens 11 (i.e., the optical axis of the relay optical system 16).

In this case, since the first camera unit 13 and the second camera unit 14 are kept stationary, such as keeping the plane where the optical axis of the first camera unit 13 and the optical axis of the second camera unit 14 are located always in the horizontal direction, so that the orientation of the target image captured by the first camera unit 13 and the second camera unit 14 remains unchanged (such as always in the upright direction), so that the observer can observe the image that is in the upright direction all the time.

Figure 18:
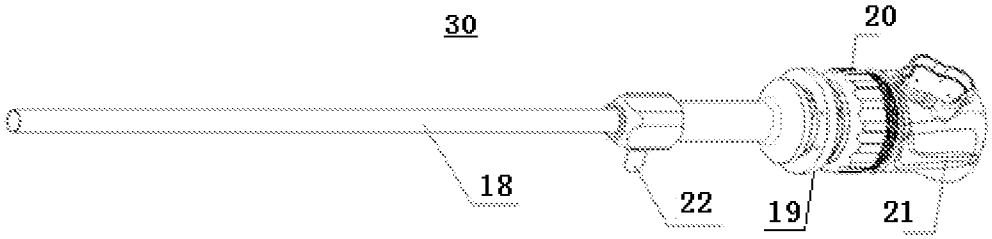
FIG. 18 is a schematic diagram of the external structure of the 3D endoscope shown in FIG. 17.

Referring to FIG. 18, on the basis of the 3D endoscope 10 shown in FIG. 17, it may also include: an insertion tube 18, a concave lens support 19, a camera unit support 20 and a handle 21.

The objective lens 15, the relay optical system 16 and the eye lens 11 are disposed in the insertion tube 18, wherein the objective lens 15 is disposed in the distal end of the insertion tube 18, the eye lens 11 is disposed in the proximal end of the insertion tube 18, and the relay optical system 16 is disposed between the objective lens 15 and the eye lens 11. By rotating the insertion tube 18, the objective lens 15, the relay optical system 16 and the eye lens 11 can be rotated.

The first end of the concave lens support 19 is connected to the proximal end of the insertion tube 18, and the concave lens 12 is disposed in the concave lens support 19.

The first end of the camera unit support 20 is connected to the second end of the concave lens support 19; the first camera unit 13 and the second camera unit 14 are disposed side by side in the camera unit support 20. The handle 21 is connected to the second end of the camera unit support 20.

In some embodiments, the first end of the camera unit support 20 may be rotatably connected to the concave lens support 19, the camera unit support 20 may rotate around the optical axis of the concave lens support 19. In other words, while keeping the camera unit support 20 stationary, the insertion tube 18 can be rotated by an angle around the optical axis of the concave lens support 19, which can change the field of view of the objective lens 15.

In this case, since the camera unit support 20 is kept stationary, that is, the first camera unit 13 and the second camera unit 14 are kept stationary, such as keeping the plane where the optical axis of the first camera unit 13 and the optical axis of the second camera unit 14 are located always in the horizontal direction, so that the orientation of the target image captured by the first camera unit 13 and the second camera unit 14 can be kept unchanged (such as always in the upright direction), so that the observer can observe the image that is in the upright direction all the time, avoiding to rotate the insertion tube 18 around the optical axis of the concave lens 12 in order to obtain a different field of view, which will cause the obtained image to rotate accordingly, or even cause the problem of not being able to image.

In other embodiments, the camera unit support 20 may also be fixedly connected with the concave lens support 19. The concave lens support 19 is rotatably connected to the proximal end of the insertion tube 18. In the case of keeping the camera unit support 20 and the concave lens support 19 stationary, the insertion tube 18 can be rotated by an angle around the optical axis of the concave lens support 19, which can change the field of view of the objective lens 15, and can also make the orientation of the target image captured by the first camera unit 13 and the second camera unit 14 remain unchanged (such as always in the upright direction), so that the observer can observe the image that is in the upright direction all the time.

In order to provide illumination to the objective lens 15 at the distal end of the endoscope insertion tube 18, in some embodiments, an optical fiber for illumination is disposed in the insertion tube 18.

In one example, an optical fiber mount 22 may be provided on the insertion tube 18, and the optical fiber mount 22 is provided with a through-hole. The insertion tube 18 is provided with an optic fiber hole connected to the through-hole on the optical fiber mount, and an optical fiber for illumination may be threaded through the through-hole and the optic fiber hole.

The axial distance between the concave lens and the eye lens 11 is also adjustable. Operating the concave lens can cause the concave lens to move towards or away from the eye lens 11 in the housing to adjust the distance between the concave lens and the eye lens 11.

The eye lens 11 may be disposed in a cylindrical housing together with the concave lens, the first camera unit 13 and the second camera unit 14, or the concave lens, the first camera unit 13 and the second camera unit 14 may be disposed together in a cylindrical housing, and the eye lens 11 is disposed in another cylindrical housing.

One or more embodiments of the present application can be applied to departments related to endoscopy, and can also be used instead of existing operating microscopes. Compared with existing surgical microscopes, in one or more embodiments of the present application, the field of view of the objective lens may be greater than 50 degrees, and more spatial ranges can be seen during surgery than existing surgical microscopes, thus enabling obtain more information on the site being observed.

Each embodiment in this specification is described in a related manner, the same and similar parts of each embodiment may be referred to each other, and each embodiment focuses on the differences from other embodiments.

The above is only a specific embodiment of the present application, but the scope of protection of the present application is not limited thereto. Any change or replacement that may be easily thought of within the scope of the technology disclosed by the present application by a person skilled in the art shall be covered by the scope of protection of the present application. Therefore, the protection scope of the present application should be based on the protection scope of the claims.

What is claimed is:

1. An optical 3D endoscope, comprising:

an objective lens, disposed at a distal end of the endoscope, for collecting the light reflected by a target object to be observed outside the distal end of the endoscope;

a relay optical system, disposed on an image side of the objective lens, for transmitting the light collected by the objective lens at the distal end of the endoscope to a magnifying unit;

the magnifying unit, disposed on an image side of the relay optical system, for transmitting the light collected by the objective lens at the distal end of the endoscope transmitted by the relay optical system to a first camera unit and a second camera unit;

the first camera unit and the second camera unit are disposed side by side on an image side of the magnifying unit, and clear apertures of the first camera unit and the second camera unit are located within a spot range of the emergent light of the magnifying unit; wherein, the first camera unit is used for receiving the light collected by the objective lens at the distal end of the endoscope transmitted by the magnifying unit, and generating a first image of the target object based on the light; and the second camera unit is used for receiving the light collected by the objective lens at the distal end of the endoscope transmitted by the magnifying unit, and generating a second image of the target object based on the light, wherein the first camera unit comprises a first camera lens and a first imaging sensor; the magnifying unit and the first camera lens form a first magnification device, for forming the first image on the first imaging sensor with the light collected by the objective lens at the distal end of the endoscope transmitted by the optical system; the first image is a magnified image of the target object;

the second camera unit comprises a second camera lens and a second imaging sensor; the magnifying unit and the second camera lens form a second magnification device, for forming the second image on the second imaging sensor with the light collected by the objective lens at the distal end of the endoscope transmitted by the optical system; the second image is a magnified image of the target object.

2. The 3D endoscope according to claim 1, wherein the first camera unit and the second camera unit may rotate together around the optical axis of the magnifying unit.

3. The 3D endoscope according to claim 1, wherein an exit angle of light of the magnifying unit is more than 15°; or, an exit pupil distance of the magnifying unit is more than 5 mm; and/or, an overall optical power of the magnifying unit is negative.

4. The 3D endoscope, comprising:

an objective lens, disposed at a distal end of the endoscope, for collecting the light reflected by the target object to be observed outside the distal end of the endoscope;

a relay optical system, disposed on an image side of the objective lens, for transmitting the light collected by the objective lens at the distal end of the endoscope to a magnifying unit;

the magnifying unit, disposed on an image side of the relay optical system, for transmitting the light collected by the objective lens at the distal end of the endoscope transmitted by the relay optical system to a first camera unit and a second camera unit;

the first camera unit and the second camera unit are disposed side by side on the image side of the magnifying unit, and clear apertures of the first camera unit and the second camera unit are located within a spot range of the emergent light of the magnifying unit; wherein, the first camera unit is used for receiving the light collected by the objective lens at the distal end of the endoscope transmitted by the magnifying unit, and generating a first image of the target object based on the light; and the second camera unit is used for receiving the light collected by the objective lens at the distal end of the endoscope transmitted by the magnifying unit, and generating a second image of the target object based on the light, wherein the magnifying unit comprises a first magnifying unit, a second magnifying unit and a third magnifying unit; wherein, the first magnifying unit comprises a first lens with negative focal power and a second lens with positive focal power, an image side of the first lens and an object side of the second lens are cemented to each other to form a first cemented lens;

the second magnifying unit comprises a third lens with positive focal power and a fourth lens with negative focal power, an image side of the third lens and an object side of the fourth lens are cemented to each other to form a second cemented lens;

the third magnifying unit comprises a fifth lens with negative focal power and a sixth lens with negative focal power; an image side of the fifth lens and an object side of the sixth lens are cemented to each other to form a third cemented lens.

5. The 3D endoscope, comprising:

an objective lens, disposed at a distal end of the endoscope, for collecting the light reflected by the target object to be observed outside the distal end of the endoscope;

a relay optical system, disposed on an image side of the objective lens, for transmitting the light collected by the objective lens at the distal end of the endoscope to a magnifying unit;

the magnifying unit, disposed on an image side of the relay optical system, for transmitting the light collected by the objective lens at the distal end of the endoscope transmitted by the relay optical system to a first camera unit and a second camera unit;

the first camera unit and the second camera unit are disposed side by side on the image side of the magnifying unit, and clear apertures of the first camera unit and the second camera unit are located within a spot range of the emergent light of the magnifying unit; wherein, the first camera unit is used for receiving the light collected by the objective lens at the distal end of the endoscope transmitted by the magnifying unit, and generating a first image of the target object based on the light; and the second camera unit is used for receiving the light collected by the objective lens at the distal end of the endoscope transmitted by the magnifying unit, and generating a second image of the target object based on the light, further comprising:

an insertion tube, in which the objective lens and the relay optical system are disposed, wherein the objective lens is disposed at a distal end of the insertion tube;

a magnifying unit support, a first end of the magnifying unit support is connected to a proximal end of the insertion tube, and the magnifying unit is disposed in the magnifying unit support;

a camera unit support, a first end of the camera unit support is connected to a second end of the magnifying unit support; the first camera unit and the second camera unit are disposed side by side on the camera unit support;

a handle, and the handle is connected with a second end of the camera unit support.

6. The 3D endoscope according to claim 5, characterized in that, the first end of the camera unit support is detachably connected to a second end of the magnifying unit;

wherein, the end portion of the second end of the magnifying unit support has a locking connection protrusion for inserting into the first end of the camera unit support; the first end of the camera unit support has a bayonet for accommodating the locking connection protrusion; an edge of the bayonet is provided with an elastic locking connection member;

when the first end of the camera unit support is connected to the second end of the magnifying unit, the locking connection protrusion is inserted into the bayonet, and the elastic locking connection member clips the locking connection protrusion into the bayonet.

* * * * *